(12) United States Patent
Kuka et al.

(10) Patent No.: US 8,911,432 B2
(45) Date of Patent: Dec. 16, 2014

(54) APPARATUS FOR MEDICAL TREATMENT OF TISSUE BY MEANS OF LASER LIGHT

(71) Applicants: Georg Kuka, Berlin (DE); Naim Ashraf, Bonn (DE); Torsten Hähnel, Chemnitz (DE)

(72) Inventors: Georg Kuka, Berlin (DE); Naim Ashraf, Bonn (DE); Torsten Hähnel, Chemnitz (DE)

(73) Assignee: Adavanced Fiber Tools GmbH, Mittweida (DE)

( * ) Notice: Subject to any disclaimer, the term of this patent is extended or adjusted under 35 U.S.C. 154(b) by 175 days.

(21) Appl. No.: 13/644,871

(22) Filed: Oct. 4, 2012

(65) Prior Publication Data

US 2013/0131657 A1    May 23, 2013

Related U.S. Application Data

(60) Provisional application No. 61/561,584, filed on Nov. 18, 2011.

(51) Int. Cl.
| | |
|---|---|
| *A61B 18/22* | (2006.01) |
| *G02B 6/02* | (2006.01) |
| *G02B 6/26* | (2006.01) |
| *G02B 6/255* | (2006.01) |

(52) U.S. Cl.
CPC ............ *A61B 18/22* (2013.01); *G02B 6/02342* (2013.01); *A61B 2018/2244* (2013.01); *G02B 6/262* (2013.01); *A61B 2018/2227* (2013.01); *G02B 6/2552* (2013.01); *A61B 2018/2288* (2013.01)
USPC .................... 606/15; 606/16; 606/17; 385/16; 385/33; 385/117; 385/125

(58) Field of Classification Search
CPC ............ A61B 18/18; G02B 6/26; G02B 6/28; G02B 6/42; G02B 6/32; G02B 6/06; G02B 6/02
USPC ............. 606/15–17, 29; 385/16–33, 117, 125
See application file for complete search history.

(56) References Cited

U.S. PATENT DOCUMENTS

| | | | |
|---|---|---|---|
| 4,310,339 A | * | 1/1982 | Blankenship ............... 65/416 |
| 5,320,620 A | | 6/1994 | Long et al. |

(Continued)

FOREIGN PATENT DOCUMENTS

DE    196 04 678 A1    12/2010

OTHER PUBLICATIONS

Kirchhof, J [et al.]: Hochleistungs-Laserfasern und photonische Mikrostrukturen, (high-performance laser fibers and photonic microstructures), Institute for Physical High Technology, Jena, Dept. Optics, in: Presentation at DGG Glasforum, Mar. 10, 2005, Wuerzburg, Germany, URL: http://www.hvg-dgg.de/uploads/media/Fa705a-Kirchhof.pdf.

*Primary Examiner* — William Thomson
*Assistant Examiner* — Victor Shapiro
(74) *Attorney, Agent, or Firm* — Henry M Feiereisen LLC

(57) ABSTRACT

An apparatus for medical treatment by means of laser light includes an optical conducting fiber which has a curved light emission end and includes a core, a cladding arranged above the core for conducting laser light coupled into the optical conducting fiber, and capillaries arranged in the cladding, wherein the capillaries run in a longitudinal direction of the optical conducting fiber at a radial distance from a longitudinal axis of the optical conducting fiber and form a capillary ring when viewed in cross-section, wherein the capillaries have cavities which are separated by bridges which have a width which is smaller than a wavelength of the laser light, wherein the laser light emerges from a forward surface of the light emission end and is transmitted in a direction which runs transverse to a substantially straight longitudinal section located directly in front of a curvature which defines the curved light emission end.

7 Claims, 2 Drawing Sheets

(56) References Cited

U.S. PATENT DOCUMENTS

| | | | |
|---|---|---|---|
| 5,495,541 A | 2/1996 | Murray et al. | |
| 6,393,178 B2* | 5/2002 | Ranka et al. | 385/28 |
| 6,654,522 B2* | 11/2003 | Chandalia et al. | 385/48 |
| 6,921,216 B1* | 7/2005 | Li et al. | 385/96 |
| 7,167,622 B2* | 1/2007 | Temelkuran et al. | 385/123 |
| 2007/0104431 A1* | 5/2007 | Di Teodoro et al. | 385/123 |
| 2009/0287198 A1* | 11/2009 | Hanley et al. | 606/15 |
| 2009/0299352 A1* | 12/2009 | Zerfas et al. | 606/15 |

* cited by examiner

APPARATUS FOR MEDICAL TREATMENT OF TISSUE BY MEANS OF LASER LIGHT

CROSS-REFERENCES TO RELATED APPLICATIONS

This application claims the benefit of prior filed U.S. provisional Application No. 61/561,584, filed Nov. 18, 2011, pursuant to 35 U.S.C. 119(e), the disclosure of which is incorporated herein by reference.

This application claims the priority of German Patent Application, Serial No. 10 2011 118 875.8, filed Nov. 19, 2011, pursuant to 35 U.S.C. 119(a)-(d), the disclosure of which is incorporated herein by reference.

BACKGROUND OF THE INVENTION

The present invention relates to a Apparatus for medical treatment, in particular of tissue by means of laser light The following discussion of related art is provided to assist the reader in understanding the advantages of the invention, and is not to be construed as an admission that this related art is prior art to this invention.

Applicators for medical treatment of living tissue with the help of lasers are known. In particular, the surgical removal or reduction in volume of prostate tissue by means of laser light is known. Holmium lasers are used as the light source, which generate strong light output at an emission wavelength (light wavelength) in the micrometer range (approx. 2123 nm), which makes very good tissue ablation possible. For this purpose, the laser light is coupled into one end of a multimode optical conducting fiber that where possible comprises a large numerical aperture (NA), and re-emerges from the forward surface of the other end. The optical conducting fiber usually terminates in a distal end piece at the straight (longitudinally aligned) light emission end, so that the laser light is emitted from its forward surface.

Because of its optical wavelength, the light from the holmium laser is absorbed strongly by water, whereby the water-bearing prostate tissue is evaporated when irradiated. The minor penetration depth into the tissue of less than one millimeter results in very thin incisions when the prostate tissue is contacted directly by the optical fiber or by the associated distal end piece, therefore immediately ablating the tissue. Visual verification may be performed with an endoscope.

In order to conduct light, the optical conducting fiber comprises a central core, which is primarily composed of quartz glass. At least one cladding (glass sheath) is arranged over the core, as well as a plastic sheath over this for protection.

A disadvantage in the treatment is that the laser light is not emitted laterally from the optical conducting fiber, but rather from the forward surface in the direction of the fiber's longitudinal axis.

It would therefore be desirable and advantageous to provide an apparatus (applicator) for medical treatment, in particular for the removal and reduction of living tissue, by means of an optical conducting fiber that is then in contact (contact mode) with the tissue, and in which the laser light is emitted with virtually no loss in a direction transverse to the principally straight longitudinal extent of the optical conducting fiber. The living tissue is especially prostate tissue.

SUMMARY OF THE INVENTION

According to one aspect of the present invention, an apparatus for medical treatment by means of laser light includes an optical conducting fiber having a curved light emission end and comprising a core, a cladding arranged above the core for conducting laser light coupled into the optical conducting fiber, and capillaries arranged in the cladding, wherein the capillaries run in a longitudinal direction of the optical conducting fiber at a radial distance from a longitudinal axis of the optical conducting fiber and form a capillary ring when viewed in cross-section, wherein the capillaries have cavities which are separated by bridges which have a width which is smaller than a wavelength of the laser light, wherein the laser light emerges from a forward surface of the light emission end, and wherein the laser light is transmitted in a direction which runs transverse to a substantially straight longitudinal section located directly in front of the curvature of the curved light emission end. The emission direction is herein the direction toward which the associated end surface faces. When the light emission end is curved, the capillaries running parallel to the core cause the laser light to be emitted at the forward surface only when the separation (the width of the division) is sufficiently small.

It is technically simple when the light emission end of the optical conducting fiber terminates with curvature, i.e., ends within the curve.

The light emission may be improved when a distal end piece is arranged on the light emission surface of the curvature, so that the laser light is emitted from the end piece. The end piece is arranged directly after the forward surface of the corresponding optical conducting fiber.

According to another advantageous feature of the invention, the capillaries are closed, in particular by the distal end piece.

A simple and technically sound embodiment provides that the distal end piece is formed by melting the optical conducting fiber at the light emission end, and then grinding and polishing it.

The light conduction in the area of the curvature can be improved when the optical conducting fiber has multiple capillary rings.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
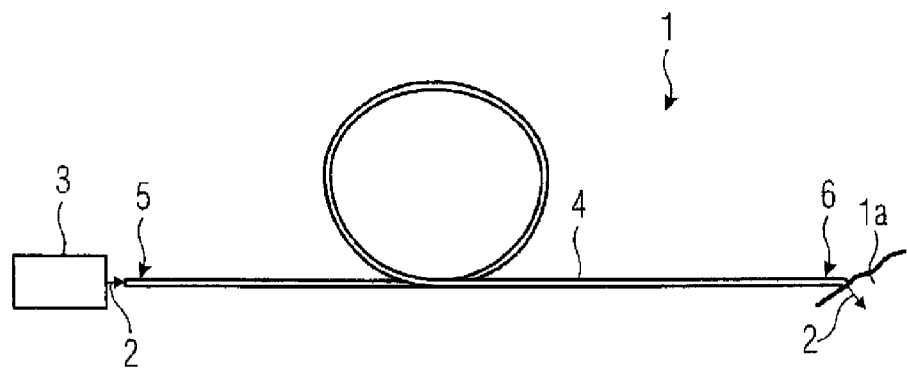
FIG. 1 shows an applicator with a holmium laser in a schematic representation.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic representation of an applicator 1 (treatment apparatus) for medical treatment, especially of living prostate tissue 1a. The treatment is performed with the help of laser light 2, which is generated by a holmium laser 3. The laser light 2 is conducted to the treatment location by means of a microstructured multimode optical conducting fiber 4 with a numerical aperture (NA) of 0.6, wherein it is coupled in a known manner (shown here only schematically) into one end 5 of the optical conducting fiber 4, and is re-emitted from the forward surface of the opposite end (the light emission end 6).

Figure 2:
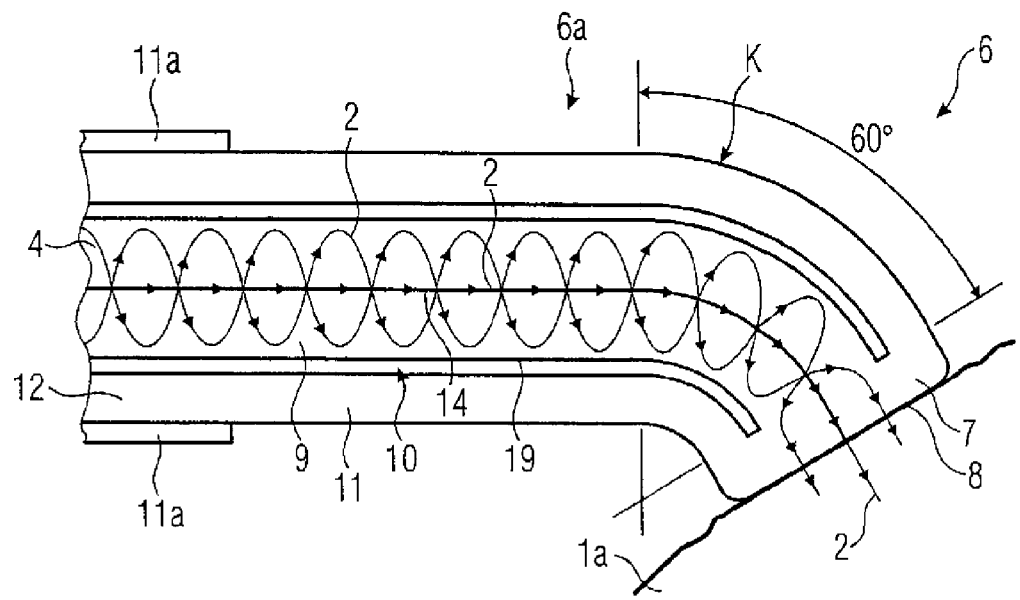
FIG. 2 shows the light emission end together with the straight section preceding it.

The light emission end 6, together with the (principally) straight lengthwise section 6a of the microstructured optical conducting fiber 4 directly preceding it, is shown schematically in FIG. 2. The optical conducting fiber 4 includes a hooked shape at its end, whereby the lengthwise section 6a forms the hook's shank and the light emission end 6 forms a curved and thus transversely extending hooked section. The hook shank is straight with respect to the curved shape (curvature) of the hook section.

The optical conducting fiber 4 includes a core 9, composed of quartz glass, over which a cladding 10 (mantle) is located. Here the cladding 10 is again coated with quartz glass 11, to increase the stability of the light emission end 6, including the lengthwise section 6a (the distal end) located directly before it. The quartz glass 11 is coated with a plastic sheath 11a, which however does not extend to the light emission end 6.

The coupled laser light 2 proceeds primarily through the core 9 of the optical conducting fiber 4 to its light emission end 6. The cladding 10 includes capillaries 12 running along the fiber's longitudinal direction and lying next to one another, each of which is arranged with a radial separation from the outer surface of the cladding 13 on the core 9, or from the longitudinal axis 14 of the optical conducting fiber 4.

The light emission end 6 is bent in this case at an angle of 60 degrees with respect to the lengthwise section 6a, with a relatively small bending radius, thus provided with a curvature K, so that the direction of the emitted laser light 2 is transverse to the longitudinal direction of the straight lengthwise section 6a, thus transverse to the non-curved section of the optical conducting fiber 4 lying immediately preceding the curvature K. The curvature K can be manufactured by bending the end 6 after heating it, for example in an arc lamp, whereby the capillaries 12 surprisingly do not collapse.

A distal end piece 7 connects directly onto the optical conducting fiber 4, and together with it forms the light emission end 6, which is manufactured by melting the optical conducting fiber 4 at the end of the fiber and then grinding and polishing it. Melting the optical conducting fiber 4 is combined with removing the plastic sheath 11a at the light emission end 6. The laser light 2 is emitted from the forward surface of the end piece 7, through which the light emission end 6 is somewhat extended. The end piece 7 may of course also exhibit other end piece configurations. The direction in which the laser light 2 emerges from the forward surface of the end piece 7 is principally transverse to the forward surface of the emission surface 8. Without the end piece 7, the laser light 2 would emerge directly from the forward surface of the optical conducting fiber 4, which is fundamentally also possible.

Figure 3:
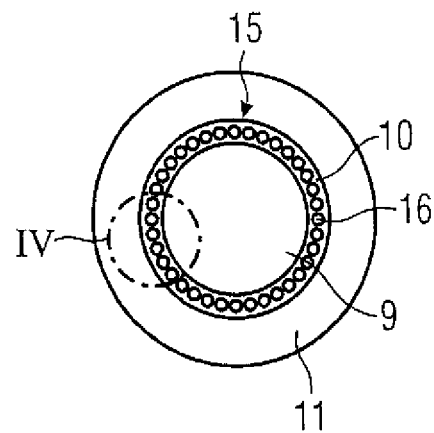
FIG. 3 shows a cross-section of the optical conducting fiber.

FIG. 3 shows a cross-section of the optical conducting fiber 4. When viewed in cross section, the capillaries 12 form a ring (capillary ring 15) of adjacent cavities (capillary cavities 16) around the longitudinal axis 14 of the optical conducting fiber 4. In principle multiple capillary rings 15 may be present.

Figure 4:
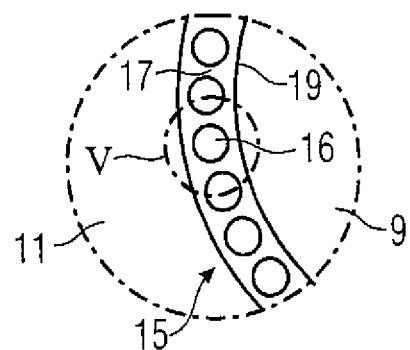
FIG. 4 shows a detail section of the cross-section shown in FIG. 3.

The detailed section IV of the capillary ring 15 from FIG. 3 is shown enlarged in FIG. 4. FIG. 4 shows that the capillary cavities 16 of the capillary ring 15 are separated by bridges 17.

Figure 5:
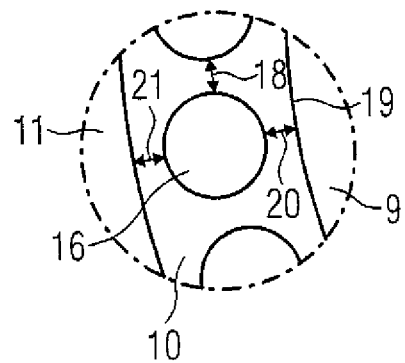
FIG. 5 shows a detail section of the section shown in FIG. 4.

The detail section V from FIG. 4 is shown enlarged in FIG. 5. The width 18 of the bridges 17 is about 1 micron, and is thus smaller than the wavelength (of about 2 microns) of the laser light 2. The radial separation 20 of the cavities 16 from the outer surface 19 of the core 9, as well as the radial separation 21 from the quartz glass 11 is here approximately equal to the bridge width 18, but they 20, 21 may also amount to many multiples of the bridge width 18.

Because of the capillary ring 15, no light is emitted laterally from the optical conducting fiber 4, despite the strong curvature K. The capillaries running parallel to the core cause the laser light 2 to be emitted only at the forward surface, even when the light emission end 6 is curved strongly, albeit only given the condition fulfilled here, that the bridge width 18 is smaller than the wavelength of the laser light 2. The direction in which the laser light 2 is emitted runs transversely with an angle of 60 degrees to the (at least within the lengthwise section 6a) principally straight optical conducting fiber 4. During treatment, the optical conducting fiber 4 and therefore the lengthwise section 6a is typically shifted along the longitudinal direction of the lengthwise section 6a, as well as rotated around its longitudinal axis, whereby the forward side emission surface 8 is located in contact (contact mode) with the prostate tissue 1a.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. An apparatus for medical treatment by means of laser light, comprising:
   an optical conducting fiber having a curved light emission end and comprising a core, a cladding arranged above the core for conducting laser light coupled into the optical conducting fiber, and capillaries arranged in the cladding, wherein said capillaries run in a longitudinal direction of the optical conducting fiber at a radial distance from a longitudinal axis of the optical conducting fiber and form at least one capillary ring when viewed in cross-section, wherein said capillaries have a light-emitting melt shut end and have cavities which are separated by bridges, said bridges having a width which is smaller than a wavelength of the laser light, wherein the laser light emerges from a forward surface of the light emission end, and wherein the laser light is transmitted in a direction which runs transverse to a substantially straight longitudinal section located directly in front of a curvature of the curved light emission end.

2. The apparatus of claim 1, further comprising a distal end piece arranged on a light emission side of the curvature, with the laser light being emitted from the distal end piece.

3. The apparatus of claim 2, wherein the distal end piece is polished and ground.

4. The apparatus of claim 2, wherein the distal end piece is formed by melting the optical conducting fiber at the light emission end, and subsequently grinding and polishing.

5. The apparatus of the claim 1, wherein the optical conducting fiber comprises multiple capillary rings.

6. The device of claim 1, wherein the capillaries extend over the curvature up to the closed light emission end.

7. An apparatus for medical treatment by means of laser light, made by the following process steps:
   providing an optical conducting fiber comprising a core, a cladding arranged above the core for conducting laser light coupled into the optical conducting fiber, and capillaries arranged in the cladding, said capillaries running in a longitudinal direction of the optical conducting fiber at a radial distance from a longitudinal axis of the optical conducting fiber and forming at least one capillary ring when viewed in cross-section, wherein said capillaries have cavities which are separated by bridges, said bridges having a width which is smaller than a wavelength of the laser light;

melting the capillaries shut at a light emission end of the optical conducting fiber thereby generating a light-emitting melt shut end of the capillaries; and bending the optical conducting fiber at the light emission end thereby forming a curved light emission end of the optical conducting fiber, wherein the laser light emerges from a forward surface of the curved light emission end, and wherein the laser light is transmitted in a direction which runs transverse to a substantially straight longitudinal section located directly in front of a curvature of the curved light emission end.

\* \* \* \* \*